United States Patent [19]

Hargis

[11] Patent Number: 4,613,705

[45] Date of Patent: Sep. 23, 1986

[54] CATALYTIC ALKYLATION OF AROMATIC AMINES WITH ALKANOLS

[75] Inventor: Duane C. Hargis, Baton Rouge, La.

[73] Assignee: Ethyl Corporation, Richmond, Va.

[21] Appl. No.: 624,533

[22] Filed: Jun. 25, 1984

[51] Int. Cl.[4] .............................................. C07C 85/24
[52] U.S. Cl. .................................... 564/409; 564/401; 564/402
[58] Field of Search ............... 564/409, 401, 402, 399, 564/474, 479, 480

[56] References Cited

U.S. PATENT DOCUMENTS 4,183,868  1/1980  Radimerski et al. ................. 564/399
4,351,958  9/1982  Takahata et al. .................... 564/409

FOREIGN PATENT DOCUMENTS 75029  6/1974  Japan .
90227  7/1978  Japan .

OTHER PUBLICATIONS

Ind. and Eng. Chem., 43, pp. 1579–1583, (1951).
Nippon Kagaku Kaishi, 1979, No. 11, pp. 1453–1457.

*Primary Examiner*—Natalie Trousof
*Assistant Examiner*—Joseph A. Boska
*Attorney, Agent, or Firm*—John F. Sieberth; Donald L. Johnson

[57] ABSTRACT

Aromatic amines are alkylated by reaction with an alcohol in the presence of a Group V-B metal oxide alkylation catalyst, preferably a major proportion of a Group V-B metal oxide such as $V_2O_5$ in combination with a minor proportion of an A-subgroup metal oxide such as $SnO_2$, so that alkylation of the aromatic amine occurs. Under most reaction conditions a considerable portion of the alcohol alkylating agent such as ethanol not consumed in the alkylation reaction passes through the reaction zone undecomposed and thus can be readily recovered for recycle or other use.

12 Claims, No Drawings

CATALYTIC ALKYLATION OF AROMATIC AMINES WITH ALKANOLS

FIELD

This invention relates to an improved catalytic process for the alkylation of aromatic amines.

BACKGROUND

Numerous methods and catalysts have been described for alkylating aromatic amines to provide valuable and useful chemical products. Among the vast literature on the general subject are some investigations on the use of certain metal oxides as the catalyst and alcohols as the alkylating agent.

Mailhe et al, *Compt. rend.*, 166, 467 (1918), report that while thoria and zirconia are effective as catalysts for the N-methylation of aniline with methanol, alumina is a superior catalyst for this reaction. Six years later Brown et al reported in *J. Am. Chem. Soc.*, 46, 1836 (1924) that silica gel was also effective as a catalyst for the N-alkylation of aniline with methanol, ethanol, propanol and butanol at 300°–500° C.

A group of catalysts for the alkylation of aniline with methanol or ethanol was studied by Shuikin and co-workers, *J. Gen. Chem.* (U.S.S.R.) 4, 1451–7 (1934) and ibid., 6, 774–9 (1936). The catalysts studied were $Al_2O_3$, $Fe_2O_3$, $Al_2O_3$—$Fe_2O_3$, $Al_2O_3$—$SnO$, $Al_2O_3$—$Cr_2O_3$, $Al_2O_3$—$NiO$ and $Al_2O_3$—$ZnO$.

Heinemann U.S. Pat. No. 2,515,872 describes a method for producing secondary and tertiary amines, which comprises contacting an aliphatic alcohol of from 1 to 20 carbon atoms and an aromatic amine containing at least one hydrogen atom bonded to the amino nitrogen atom, at a temperature between 450° F. and 600° F. with bauxite thermally activated at 1000° F. to 1200° F. and containing from 4% to 22% of naturally occurring iron oxide.

A further study of the alkylation of aniline with methanol is reported by Hill et al in *Ind. & Eng. Chem.*, 43, 1579–83 (1951). They found that as possible catalysts for the reaction tungstic oxide was not very effective, zinc oxide, chromium oxide and magnesium oxide exerted little influence on the reaction, thorium oxide had little or no activity and that titanium oxide was moderately active. They also found that most of these oxides, including titania, tended to decompose the alcohol reactant.

U.S. Pat. No. 2,580,284 to Deahl et al., describes the production of secondary aromatic amines from primary aromatic amines and alcohols using catalysts that comprise as essential components, metallic copper, alumina and at least one other difficultly reducible oxide. In order of decreasing preference these other oxides are indicated to be calcium oxide, zinc oxide, chromium oxide, magnesium oxide, ferrous oxide, cadmium oxide, and potassium oxide. The patentees also refer to runs involving a feed mixture of aniline, methanol and hydrogen (1:1:2 moles), and the following catalysts (the proportions of which are unspecified): copper, manganese oxide, alumina, and "catalysts containing the oxides of . . . strontium, molybdenum or vanadium." Substitution of nickel or silver for metallic copper in the Deahl et al. catalysts is shown to result in very poor conversions, as did the replacement of the alumina with a diatomaceous earth.

Inoue et al, *Sekiyu Gakkai Shi* 15, No. 5, 372–8 (1972), describe the methylation of aniline and o-toluidine with methanol and an aluminum oxide-magnesium oxide catalyst.

The use of copper chromite as a catalyst in the alkylation or phenylation of anilines with alcohol or phenol was investigated by Nakagawa et al—see Japan Kokai Tokkyo Koho 73-49,727 (laid open in July 1973) and 77-48,969 (laid open in December 1977).

Murai et al. U.S. Pat. No. 3,819,709 refers to the synthesis of N-methylaniline in a liquid phase reaction between aniline and methanol using a catalyst consisting of (a) copper or (b) a chromium catalyst, e.g., Cr.Cu.O, Cr.Zn.O, Cr.Ni.O, Cr.Fe.O, Cr.Mo.O, Cr.Cu.BaO, Cr.Cu.Mn.O, etc., in which the chromium content is 20–80 weight percent, the Cu, Zn, Mi, Fe or Mo content is 20–80 weight percent, and the content of Ba, Ca, Mg or Mn is 0–5 weight percent.

Catalytic ring alkylation of phenylamines with alcohols using an alumina and molybdenum oxide catalyst is described in U. S. Pat. No. 3,868,420 (granted in February 1975 to Evans et al).

Takamiya et al in *Waseda Daigaku Rikogaku Kenkyusho Hokoku* 69, 21–25 (1975) report the results of the study of the vapor phase catalytic N-methylation of aniline with methanol with certain transition metal zeolites as catalysts. They found that the catalytic activity of the metal ion was $Zn^{2+} > Co^{2+} > Ni^{2+} > Mn^{2+} > Cu^{2+}$.

Matsumoto et al., Japan Kokai Tokkyo Koho 76-75029 (laid open in June 1976) describes nuclear methylation of xylidine with methanol using as catalyst alumina-silver oxide, silica alumina-silver oxide, alumina-chromium oxide, alumina-vanadium oxide, titanium oxide-zinc oxide or titanium oxide-zirconium oxide.

Japan Kokai Tokkyo Koho 78-90227 (laid open in August 1978) to Motoyama et al teaches the use of silica-alumina as the catalyst for reaction between primary aromatic amines with alcohols or ethers.

In U.S.S.R. Patent No. 644,526 (issued in January 1979 to Dobrovol'skii et al) catalysts containing copper oxide, barium oxide, chromium oxide and titanium oxide for alkylation of aromatic amines with alcohols are described.

U.S.S.R. Patent No. 666,167 (issued in June 1979 to Esipov et al) refers to the use of nickel oxide as a catalyst for the alkylation of aniline with alcohols.

Takamiya et al, *Nippon Kagaku Kaishi,* 1979, No. 11, 1453–7, describe the N-methylation of aniline with methanol over a magnesium oxide catalyst.

U.S. Pat. No. 4,183,868 (granted in January 1980 to Radimerski et al) teaches the alkylation of 2,6-dialkyl anilines with alkanols using a copper oxide-chromium oxide or copper oxide-zinc oxide catalyst containing palladium or platinum. The catalyst, which may also contain small amounts of alkaline earth oxides or alkali metal oxides such as barium oxide or sodium oxide, is activated before use by heating to 120°–350° C. with hydrogen.

U S. Pat. No. 4,351,958 (granted in September 1982 to Takahata et al) describes the alkylation of aromatic amines by reaction with a primary or secondary alcohol using a catalyst containing iron oxide as the main constituent. Although the iron oxide catalysts described in the patent are generally effective, they cause extensive decomposition of the alcohol at useful reaction temperatures. Thus in practice it is not possible to recover unreacted alcohol for recycle or other use.

THE INVENTION

In accordance with this invention an efficacious process for alkylating alkylatable aromatic amines is provided. In general, the process comprises the step of reacting (a) an aromatic amine having at least one replaceable hydrogen atom on an amine group or on an aromatic ring carrying an amino group or both, with (b) an alkanol in the presence of a Group V-B metal oxide alkylation catalyst so that alkylation of the aromatic amine occurs. When effecting nuclear alkylation (i.e., alkylation on the ring), best results are achieved when the aromatic amine has at least one primary amino group on an aromatic ring and has a replaceable hydrogen on the ring in at least an ortho or para position relative to such amino group.

A preferred embodiment of this invention involves using a catalyst composed predominantly of at least one oxide of a Group V-B metal, most preferably a vanadium oxide (especially $V_2O_5$) and a minor proportion of at least one oxide of an A-subgroup metal, preferably a Group IV-A metal oxide (especially stannic oxide). These and still other preferred embodiments of this invention will be still further apparent from the ensuing description and appended claims.

A particular advantage of my process, especially when using my preferred catalysts, is that under most reaction conditions a considerable portion of the alcohol alkylating agent such as ethanol not consumed in the alkylation reaction passes through the reaction zone undecomposed and thus can be readily recovered for recycle or other use. In addition, my process involves use of catalysts which are easily prepared, and which in many cases have superior catalytic activity and long useful lives.

Another feature of this invention is that the nature of the alkylation product can be varied by adjustment of reaction conditions. In general, when an opportunity exists for both ring and nitrogen alkylation to occur, the use of higher reaction temperatures tends to promote an increase in the ring alkylation especially when using $V_2O_5$-based alkylation catalysts.

The present invention is carried out at an elevated temperature conventional for catalytic alkylation processes. The temperature of reaction for the present process is usually about 200° C. or higher, preferably 250° C. or higher. More preferably, the process of the present invention is carried out at an elevated temperature in the range of about 250°–400° C. While higher temperatures may be used, the temperature used should take into consideration the thermal decomposition temperatures of the reactants and products as well as the effect of temperature on the activity of the particular heterogeneous catalyst system being employed. In general, the most preferred temperatures for the process fall in the range of from about 275° to about 375° C.

When the process of the present invention is carried out as further described below, the conversion of aromatic amines such as aniline, toluidine, xylidine, and more complex aromatic amines is usually in the range of from less than 5 to as much as 30% or more. The 30% or more figure is considered very satisfactory for most catalytic alkylation processes. In view of the recoverability of the alkylating agent of the present invention, conversions in this range are especially advantageous since the process can be made much more economical with recovery of such a reactant. The process of the present invention is suitably carried out at atmospheric pressure but may be carried out at superatmospheric or subatmospheric pressures.

Numerous aromatic amines are usable in the process of this invention. For example use may be made of single ring compounds such as aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 2,6-xylidine, 3,4-xylidine, 3,5-xylidine, 2,3-diethylaniline, 2,4-diethylaniline, 2,5-diethylaniline, 2,6-diethylaniline, 3,4-diethylaniline, 3,5-diethylaniline, 2,3-diisopropylaniline, 2,4-diisopropylaniline, 3,5-diisopropylaniline, and the like. Also usable in the process of this invention are the secondary and tertiary aromatic amines such as N-methylaniline, N-ethylaniline, N-isopropylaniline, N,N-dimethylaniline, N,N-diethylaniline, N,N-diisopropylaniline, N-methyl-o-toluidine, N-methyl-2,3-xylidine, N-methyl-2,4-xylidine, N-methyl-2,5-xylidine, N-methyl-3,5-xylidine, N,N-dimethyl-o-toluidine, N,N-dimethyl-m-toluidine, N,N-dimethyl-p-toluidine, N,N-dimethyl-2,3-xylidine, N,N-dimethyl-2,4-xylidine, N,N-dimethyl-2,5-xylidine, N,N-dimethyl-3,5-xylidine, N-ethyl-o-toluidine, N-ethyl-m-ethylaniline, N-ethyl-p-ethylaniline, N-ethyl-2,3-diethylaniline, N-ethyl-2,4-diethylaniline, N-ethyl-2,5-diethylaniline, N-ethyl-3,5-diethylaniline, N,N-diethyl-o-ethylaniline, N-ethyl-3,5-diethylaniline, N,N-diethyl-o-ethylaniline, N,N-diethyl-m-ethylaniline, N,N-diethyl-p-ethylaniline, and the like. Also usable according to the process of the present invention are multiple ring compounds such as diphenylamine, 4-aminobiphenyl, 1-naphthylamine, 2-naphthylamine, 1-anthrylamine, 1-phenanthrylamine, and the like. Similarly the aromatic diamines, triamines, and other polyamines are usable. Examples of such compounds include 2,4-toluenediamine, 2,5-toluenediamine, 1,3-diaminobenzene, 1,4-diaminobenzene, 4,4'-methylenebisaniline, 1,3,5-triaminobenzene, 1,4-diaminonaphthalene, 1,5-diaminonaphthalene, and the like.

Of the above described aromatic amines, the single ring aromatic amines are preferred. Aniline and ring alkylated anilines are the more preferred of the single ring aromatic amines. Most preferred are aniline, one or a mixture of two or more toluidine isomers or one or a mixture of two or more xylidine isomers.

Various alcohols and mixtures of alcohols are usable according to the present invention. These include aliphatic alcohols and alicyclic alcohols. Useful aliphatic alcohols include alkanols, alkenols, alkynols, cycloalkylcarbinols and arylalkanols, such as methanol, ethanol, propanol, isopropanol, butanol, pentanol, 3-methyl-1-butanol, hexanol, 3,3-dimethyl-1-butanol, heptanol, octanol, ethanolamine, 3-amino-1-propanol, 6-amino-1-hexanol, 2-ethoxyethanol, 2-butoxyethanol, 2-(2-ethoxyethoxy)ethanol, allyl alcohol, crotyl alcohol, 3-buten-1-ol, methallyl alcohol, 3-penten-1-ol, 4-penten-1-ol, 2-hexen-1-ol, 3-hexen-1-ol, propargyl alcohol, 3-butyn-1-ol, 4-pentyn-1-ol, 5-hexyn-1-ol, cyclopropylcarbinol, cyclopentanemethanol, cyclohexylmethanol, benzyl alcohol, phenethyl alcohol, and the like. Primary alkanols are preferred. Especially preferred are methanol, ethanol and propanol.

Alicyclic alcohols usable according to the present invention include the cycloalkanols, cycloalkenols and cycloalkynols, and their ring-substituted congeners, such as cyclobutanol, cyclopentanol, cyclohexanol, cyclooctanol, 2-methylcyclobutanol, 3-methylcyclobutanol, cyclopentanol, 2-methylcyclopentanol, 3- methylcyclopentanol, cyclohexanol, cyclooctanol, cyclopentenol, cyclohexenol, cyclooctynol, and the like.

Generally speaking, most alcohols are usable according to the present invention although in some cases unreactive types may be encountered. Thus, I utilize in the present process only alcohols that are coreactive with the alkylatable aromatic amine so that alkylation occurs. In this connection, the term "alkylation" is used herein in a generic sense to indicate that an organic group from the alcohol reactant, whether open chain or cyclic, is introduced into the molecule of the aromatic amine reactant.

The present invention is capable of being carried out in either a batch or continuous operation mode according to the available equipment and intentions of the operator.

According to the invention, various catalysts may be used so long as the catalyst consists essentially of a Group V-B metal oxide of suitable activity in the alkylation reaction under consideration. As is well known, Group V-B is composed of vanadium, niobium and tantalum, and various oxides of these metals that are viable catalysts for the alkylation are within the ambit of this invention. Catalysts composed of mixtures of two or more different oxides of the same V-B subgroup metal (e.g., $V_2O_4$ and $V_2O_5$; $V_2O_3$ and $V_2O_5$; $V_2O_3$, $V_2O_4$ and $V_2O_5$; etc.) may also be used. Likewise, mixtures composed of oxides of two or all three metals of Group V-B (e.g., $V_2O_5$ and $Nb_2O_5$; $V_2O_5$ and $Ta_2O_5$; $Nb_2O_5$ and $Ta_2O_5$; etc.) may be used. Similarly, use may be made of catalysts composed of oxides of two or more metals, a major portion of which is one or more oxides of one or more Group V-B metals and a minor portion of which is one or more oxides of one or more non-Group V-B metals. Some examples of such catalysts are:

$V_2O_5$—$TiO_2$
$V_2O_5$—$ZrO_2$
$V_2O_5$—$MoO_3$
$V_2O_5$—$CrO_3$
$V_2O_5$—$WO_3$
$V_2O_5$—$MnO_2$
$V_2O_5$—$Fe_2O_3$
$V_2O_5$—$Fe_2O_3$—$GeO_2$
$V_2O_5$—$TiO_2$—$MoO_3$
$V_2O_5$—$ZrO_2$—$ZnO$
$V_2O_5$—$TiO_2$—$ZrO_2$—$HfO_2$
$Nb_2O_5$—$TiO_2$
$Ta_2O_5$—$TiO_2$
$V_2O_5$—$Ta_2O_5$—$ZrO_2$
$Ta_2O_5$—$MoO_3$
$Nb_2O_5$—$CrO_3$
$Nb_2O_5$—$WO_3$
$V_2O_5$—$Nb_2O_5$—$MnO_2$
$Ta_2O_5$—$Fe_2O_3$
$Nb_2O_5$—$TiO_2$—$ZnO$
$Ta_2O_5$—$Ru_2O_3$—$ZnO$
$V_2O_5$—$TiO_2$—$Fe_2O_3$.

Various other oxides usable as additional components of the catalysts of the present invention such as one or more oxides of aluminum, antimony, barium, beryllium, bismuth, calcium, cobalt, gallium, lead, magnesium, nickel, osmium, potassium, silicon, sodium, tin, and the like may be prepared by any of the known means and combined with the Group V-B metal oxide catalysts according to the invention. As noted above, catalysts composed of one or more Group V-B metal oxides in combination with one or more non-Group V-B metal oxides should predominate (on a molar basis) in the V-B subgroup metal oxide(s). In fact, such mixed oxide catalysts preferably contain at least 70 mole % of one or more Group V-B metal oxides and no more than about 30 mole % of one or more non-Group V-B metal oxides. As pointed out above, a preferred embodiment of the invention involves use of a catalyst composed predominantly of at least one oxide of a Group V-B metal and a minor proportion of at least one oxide of an A-subgroup metal. A few examples of such catalysts include:

$V_2O_5$—$Li_2O$
$V_2O_5$—$Na_2O$
$V_2O_5$—$K_2O$
$V_2O_5$—$CaO$
$V_2O_5$—$BaO$
$V_2O_5$—$Al_2O_3$
$V_2O_5$—$Tl_2O_3$
$V_2O_5$—$GeO_2$
$V_2O_5$—$Ta_2O_5$—$GeO_2$
$V_2O_5$—$TiO_2$—$Sb_2O_3$
$V_2O_5$—$ZrO_2$—$ZnO$—$Bi_2O_3$
$V_2O_5$—$TiO_2$—$ZrO_2$—$HfO_2$
$Nb_2O_5$—$GeO_2$
$Ta_2O_5$—$GeO_2$
$V_2O_5$—$Ta_2O_5$—$Al_2O_3$
$Ta_2O_5$—$MoO_3$—$GeO_2$
$Nb_2O_5$—$CrO_3$—$MgO$
$Nb_2O_5$—$WO_3$—$SrO$
$V_2O_5$—$Nb_2O_5$—$MnO_2$—$GeO_2$
$Ta_2O_5$—$Fe_2O_3$—$Tl_2O_3$
$Nb_2O_5$—$TiO_2$—$BeO$
$Ta_2O_5$—$Ru_2O_3$—$CaO$
$Nb_2O_5$—$ZrO_2$—$HfO_2$—$GeO_2$.

Particularly preferred metal oxide combinations of this type are exemplified by the following:

$V_2O_5$—$SnO_2$
$Nb_2O_5$—$SnO_2$
$Ta_2O_5$—$SnO_2$
$V_2O_5$—$Nb_2O_5$—$SnO_2$
$V_2O_5$—$Ta_2O_5$—$SnO_2$
$Nb_2O_5$—$Ta_2O_5$—$SnO_2$
$V_2O_5$—$Nb_2O_5$—$Ta_2O_5$—$SnO_2$
$V_2O_5$—$TiO_2$—$SnO_2$
$V_2O_5$—$GeO_2$—$SnO_2$
$V_2O_5$—$Ta_2O_5$—$GeO_2$—$SnO_2$
$V_2O_5$—$MoO_3$—$SnO_2$
$V_2O_5$—$ZnO$—$SnO_2$
$V_2O_5$—$MnO_2$—$SnO_2$.

Methods for the manufacture of metal oxides are known and reported in the literature. When utilizing such procedures care should be taken to avoid heating the oxide catalyst to a temperature which destroys or substantially diminishes its catalytic activity in my alkylation process. The catalyst may be supported on or impregnated onto a suitable inert carrier although this is ordinarily unnecessary.

Although the process can be carried out in the liquid phase, it is preferable to conduct the process in the vapor phase using a fixed-bed or a moving or fluidized bed of the catalyst.

The present invention will be still further understood by a review of the following illustrative example of the best mode of the invention of which I am now aware, in which all of the percentages are expressed on a weight basis.

In each of the runs referred to hereinafter, use was made of a tubular reactor positioned within an Ohio Thermal wire wound tubular furnace, Model T11C-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor itself was a 19 inch long, 1 inch inside diameter stainless steel tube fitted with an internal thermocouple well. The reactor tube was fitted for supply of helium gas from one line and a second line connected to a Milton Roy pump. The second line fed reactants from a reservoir attached thereto. A water condenser below the reactor tube and an ice bath were used to collect liquid in glassware in the ice bath. The vapors transmitted from the glassware in the ice bath were directed to a dry ice bath and the outlet thereof was connected directly to a gas chromatography unit and then to a wet test meter.

In each of the runs referred to hereinafter, the following procedure was used. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to good standard laboratory practice. The desired feed for the run was added to the reservoir and the pump and inlet tube as necessary. The ice water bath and dry ice bath were attached, and the helium flush was started at the rate of 20-30 cc per minute during furnace warmup and stabilization. To start a run, the helium was turned off, and the feed pump was turned on at the desired feed rate. The thermocouple temperatures were recorded along with the feed level and the wet test meter readings. The sampling times were also noted. The product gases were directed to the sample loop of the GC sampling valve and injected onto a 10′×⅛″ Poropak ™ R column. The traps were removed and immediately replaced with a second set. The liquid samples were combined and weighed. To terminate the run, the feed pumps were turned off and drained for about five minutes before removing the residue therein. Thereafter, the helium flush was again turned on at about 20-30 cc per minute and the furnace was turned off. After cooling to room temperature, the reactor tube was removed for catalyst inspection, analysis, and/or replacement.

EXAMPLE

Catalyst Preparation

A solution was prepared by dissolving 11.4 g $SnCl_2$ plus 3 mL concentrated HCl in 100 mL distilled $H_2O$ which was subsequently neutralized to pH7 with 14% $NH_4OH$ to precipitate $Sn(OH)_2$. The $Sn(OH)_2$ was filtered and washed free of chloride ion with distilled $H_2O$. The $Sn(OH)_2$ precipitate was added to an aqueous mixture of 70.3 g $NH_4VO_3$ and 48.8 g oxalic acid in 300 mL $H_2O$. To this mixture was added 14% $NH_4OH$ to pH 10. The dark black precipitate was filtered and washed with distilled $H_2O$. The gel was extruded through a 50 cc plastic syringe, air-dried, oven-dried at 100° C. for 2 hours, then calcined at 450° C. overnight to give 46.2 g finished catalyst. Its composition was 85.8 weight % $V_2O_5$ and 14.2 weight % $SnO_2$.

Alkylation Reactions

Using the apparatus and procedure described above, aniline and ethanol were reacted in the vapor phase over this catalyst at 300° C. (Run 1) and at 350° C. (Run 2). The reactants were employed in a ratio of 5.0 moles of ethanol per mole of aniline. The alkylations were conducted using a liquid hourly space velocity (LHSV) of 0.2 hr$^{-1}$. The results of these runs are set forth in the Table. The gaseous products referred to therein are uncondensables, and the magnitude of this figure serves as an indication of the extent of decomposition that occurred during the run.

TABLE

|  | Run Number | |
|---|---|---|
|  | 1 | 2 |
| Alkylation of Aniline with Ethanol | | |
| Temperature, °C. | 300 | 350 |
| Aniline Conversion, % | 34 | 84 |
| Ethanol Conversion, % | 56 | 100 |
| Product Distribution, wt. percent | | |
| N-et aniline | 74.0 | 15.4 |
| o-et aniline | 6.4 | 2.2 |
| Di-et anilines | — | 5.8 |
| Others | 19.6* | 76.7* |
| N—alkylation, % | 74.0 | 15.4 |
| Gaseous products, mL/hr | 315 | 580 |

*GC-MS indicated the presence of alkylated quinolines, acetanilide and diphenylamine In contrast to the results reported above, extensive amounts of decomposition of the alkylating agent were encountered when using an alcohol as the alkylating agent and an iron oxidegermanium oxide catalyst in accordance with the prior art. See in this connection U.S. Pat. No. 4,351,958. In particular, when ethanol and aniline were reacted in the above manner at 350° C. over a catalyst composed of 96.1 weight percent $Fe_2O_3$ and 3.9 weight percent $GeO_2$, non-condensable gases were evolved at the rate of 1800 mL/hr. In fact, no ethanol passed through the reaction zone—the ethanol which did not react with the aniline was completely destroyed.

The conditions used in the process of this invention are susceptible to considerable variation. For example, while my process is usually conducted with an excess of the alcohol reactant relative to the aromatic amine reactant, a stoichiometric deficiency of the alcohol may be used, especially when seeking to maximize monoalkylation and minimize polyalkylation. Likewise, the ratio used will be influenced to some extent by the composition of the amine (i.e., whether it is a monoamine or a polyamine), the composition of the alcohol and the extent and type of alkylation (i.e., nuclear alkylation and/or N-alkylation) desired. In most cases, the reaction mixture will contain about 0.5 to about 10 molar equivalents of the alcohol per molar equivalent of the amine. In the case of reactions between alcohols and monoamines, the molar ratio of alcohol to amine is preferably in the range of about 1:1 to about 7:1.

In conducting the process of this invention, the inclusion of water in the feed to the catalyst can be helpful insofar as the regiochemical aspects of the process are concerned. When water is employed, it will normally be used in amounts no higher than about 10 moles per mole of alcohol used, preferably in amounts falling in the range of about 0.1 to about 5 moles per mole of alcohol used.

It is possible to vary certain aspects and other features of the above described invention without departing from the lawful scope or true spirit thereof.

I claim:

1. A process for alkylating aromatic amines comprising the step of reacting (a) an aromatic amine having at least one replaceable hydrogen atom on an amine group or on an aromatic ring carrying an amino group or both, with (b) an alkanol in the presence of a mixed metal oxide alkylation catalyst consisting of at least about 70% by weight of at least one Group V-B metal oxide and up to about 30% by weight of stannic oxide so that alkylation of the aromatic amine occurs and so that at least a substantial portion of the alkanol not consumed in the alkylation reaction passes through the alkylation zone undecomposed.

2. A process of claim 1 wherein the alkanol is ethanol.

3. A process of claim 1 wherein the amine is a mononuclear primary aromatic amine having one or two amino groups on the aromatic ring.

4. A process of claim 3 wherein the amine is aniline, one or a mixture of two or more toluidine isomers or one or a mixture of two or more xylidine isomers, and the alkanol is methanol, ethanol or propanol.

5. A process of claim 1 wherein the reaction is conducted in the vapor phase by contacting a vapor phase mixture of the amine and the alkanol with a bed of the catalyst.

6. A process of claim 1 wherein the Group V-B metal oxide is composed predominantly of vanadium pentoxide.

7. A process for alkylating aromatic amines comprising the step of reacting (a) an aromatic amine having at least one primary amino group on an aromatic ring and having a replaceable hydrogen atom on the ring in at least an ortho or para position relative to such amino group, with (b) ethanol in the presence of a mixed metal oxide alkylation catalyst consisting of at least about 70% by weight of at least one Group V-B metal oxide and up to about 30% by weight of stannic oxide so that alkylation of the aromatic amine occurs and so that at least a substantial portion of the ethanol not consumed in the alkylation reaction passes through the alkylation zone undecomposed.

8. A process of claim 7 wherein the amine is a single ring aromatic amine.

9. A process of claim 7 wherein the reaction is conducted in the vapor phase by contacting a vapor phase mixture of the amine and the ethanol with a bed of the catalyst at a temperature of at least about 200° C. but below that at which the catalyst becomes inactive.

10. A process of claim 7 wherein the catalyst consists of at least about 70% by weight of vanadium pentoxide and up to about 30% by weight of stannic oxide.

11. A process of claim 10 wherein the amine is a single ring aromatic amine, and wherein the reaction is conducted in the vapor phase by contacting a vapor phase mixture of the amine and the ethanol with a bed of the catalyst at a temperature of at least about 200° C. but below that at which the catalyst becomes inactive.

12. A process of claim 11 wherein the aromatic amine is aniline.

* * * * *